(12) United States Patent
Struble (10) Patent No.: US 6,969,369 B2
(45) Date of Patent: Nov. 29, 2005

(54) IMPLANTABLE DRUG DELIVERY SYSTEM RESPONSIVE TO INTRA-CARDIAC PRESSURE

(75) Inventor: Chester Struble, Eijsden (NL)

(73) Assignee: Medtronic, Inc., Minneapolis, MN (US)

( * ) Notice: Subject to any disclaimer, the term of this patent is extended or adjusted under 35 U.S.C. 154(b) by 282 days.

(21) Appl. No.: 10/126,538

(22) Filed: Apr. 22, 2002

(65) Prior Publication Data

US 2003/0199813 A1 Oct. 23, 2003

(51) Int. Cl.[7] .............................................. A61M 31/00
(52) U.S. Cl. ................................. 604/67; 604/288.01
(58) Field of Search ............................. 604/22, 65–67, 604/93.01, 288.01, 288.02, 288.03, 288.04; 128/DIG. 12, DIG. 13

(56) References Cited

U.S. PATENT DOCUMENTS

| | | | |
|---|---|---|---|
| 3,651,806 A | | 3/1972 | Hirshberg |
| 3,923,060 A | * | 12/1975 | Ellinwood, Jr. |
| 4,003,379 A | | 1/1977 | Ellinwood, Jr. |
| 5,041,107 A | * | 8/1991 | Heil, Jr. .................. 604/891.1 |
| 5,153,178 A | | 10/1992 | Maroko |
| 5,269,301 A | | 12/1993 | Cohen |
| 5,368,040 A | | 11/1994 | Carney |
| 5,417,717 A | | 5/1995 | Salo et al. |
| 5,534,504 A | * | 7/1996 | Sollevi |
| 5,535,752 A | | 7/1996 | Halperin et al. |
| 5,558,640 A | * | 9/1996 | Pfeiler et al. ................. 604/67 |
| 5,564,434 A | | 10/1996 | Halperin et al. |
| 5,626,623 A | | 5/1997 | Kieval et al. |
| 5,810,735 A | | 9/1998 | Halperin et al. |
| 6,024,704 A | | 2/2000 | Meador et al. |
| 6,085,754 A | * | 7/2000 | Alferness et al. |
| 6,155,267 A | * | 12/2000 | Nelson ....................... 128/899 |
| 6,236,887 B1 | * | 5/2001 | Ben-Haim et al. ............. 607/3 |
| 6,409,674 B1 | * | 6/2002 | Brockway et al. .......... 600/486 |

OTHER PUBLICATIONS

Harrison's Principles of Internol Medicine, vol. 2, Chapter 214, p. 1155.*

* cited by examiner

*Primary Examiner*—Manuel Mendez
(74) *Attorney, Agent, or Firm*—Paul H. Dowall; Girma Wolde-Michael (57) ABSTRACT

The invention is directed to techniques for monitoring the condition of a patient, such as a patient having congestive heart failure, and appropriately modifying the patient's drug therapy as a function of a pressure in the patient's heart, such as the estimated pulmonary artery diastolic pressure. The drugs may be administered by an implanted drug delivery device. The drug selection, the drug dosage or both may be controlled as a function of the pressure and/or the activity level of the patient.

25 Claims, 10 Drawing Sheets

IMPLANTABLE DRUG DELIVERY SYSTEM RESPONSIVE TO INTRA-CARDIAC PRESSURE

FIELD OF THE INVENTION

The present invention relates generally to the treatment of congestive heart failure with drugs that increase cardiac output, and more particularly to the treatment of congestive heart failure with an implanted drug delivery device.

BACKGROUND

Heart failure refers to the heart's inability to keep up with the demands made upon it. Congestive heart failure refers to an inability of the heart to pump an adequate amount of blood to the body tissues. Because the heart is unable to pump an adequate amount of blood, blood returning to the heart becomes congested in the venous and pulmonary system.

In a healthy heart, the heart pumps all of the blood that returns to it, according to the Frank-Starling law. Increased venous return leads to increased end diastolic volume, which causes increased strength of contraction and increased stroke volume. In addition to intrinsic control according to the Frank-Starling law, a healthy heart is subject to extrinsic control, such as stimulation by the sympathetic nervous system to enhance contractility.

In a patient experiencing congestive heart failure, intrinsic and extrinsic control mechanisms may not function properly, and consequently the heart may fail to pump an adequate amount of blood. A condition known as cardiac decompensation is used to describe heart failure that results in a failure of adequate circulation.

Failure of the left side of the heart is generally more serious than the failure of the right side. On the left side of the heart, blood returns from the pulmonary system and is pumped to the rest of the body. When the left side of the heart fails, there are consequences to both the pulmonary system and to the rest of the body. A patient with congestive heart failure may be unable to pump enough blood forward to provide an adequate flow of blood to his kidneys, for example, causing him to retain excess water and salt. His heart may also be unable to handle the blood returning from his pulmonary system, resulting in a damming of the blood in the lungs and increasing his risk of developing pulmonary edema.

Causing more blood to be expelled from the heart, i.e., increasing cardiac output would increase the blood flow to the organs and tissues and reduce the risk of damming of blood in the lungs caused by heart failure. Patients with congestive heart failure are often treated with drug therapy intended to increase their cardiac output. Drugs administered to treat congestive heart failure by increasing cardiac output often have a positive inotropic effect on the heart. Drugs that have a positive inotropic effect on the heart increase cardiac output by increasing the contractility of the heart, which causes the heart to beat more forcefully, which in turn causes the ventricles of the heart to eject more blood per stroke. Drugs that have a positive inotropic effect on the heart include cardiac glycosides such as digitalis, digoxin and digitoxin, beta-adrenergic agonists such as dopamine and dobutamine, and phosphodiesterase inhibitors such as amrinone and milrinone.

Often, a physician determines a course of drug therapy for a patient with congestive heart failure based on the patient's condition during an admission or office visit. The drugs to be administered and the dosages for those drugs are chosen at that time. The drugs may then be self-administered or administered via an implanted drug delivery device. In some cases, congestive heart failure patients frequently visit the physician's office to have their condition evaluated. At these visits, the patient may receive a supplemental drug or dosage or otherwise have the drug therapy modified as indicated by his condition. This situation may be very costly because of the hospital stay, nursing costs, patient transportation costs, and so forth.

Further, frequent visits fail to recognize changes in the patient's condition between visits. These changes may indicate an increased or decreased need for drug therapy that increases cardiac output. Because these changes are not recognized, the drug therapy is not modified to address them. If the changes indicate a worsening of the patient's condition and a need for increased cardiac output, failure to address them promptly may endanger the patient.

Therefore, there is a need for a system and method to monitor a congestive heart failure patient's condition, and appropriately modify the patient's drug therapy as a function of the patient's condition, in an outpatient setting.

Some existing methods monitor a patient's condition with an implanted physiological sensor, and control the operation of an implanted drug delivery device as a function of the patient's condition as measured by the physiological sensor. For example, U.S. Pat. No. 4,003,379, issue to Ellinwood, Jr., discloses controlling an implanted drug delivery device to deliver hypertension medication in response to blood pressure as measured by a pressure transducer implanted in the neck or lower extremities.

Some existing methods for monitoring a patient's condition in an outpatient situation use an implanted pressure monitor and sensor to estimate the patient's pulmonary artery diastolic pressure as a function of the blood pressure in the patient's right ventricle. For example, U.S. Pat. No. 5,368,040, issued to Carney, discloses a system that includes an implanted pressure monitor that can estimate the pulmonary artery diastolic pressure from a pressure signal received from a pressure sensor in the right ventricle. Further, U.S. Pat. No. 6,155,267, to Nelson, discloses using the occurrence of a change in the state of a physiological parameter, such as estimated pulmonary artery diastolic pressure, as a trigger to change the dosage of a drug delivered by an implanted drug delivery device.

None of the existing methods, however, disclose a system and method to monitor a congestive heart failure patient's condition and appropriately modify the patient's drug therapy as a function of the patient's condition in an outpatient situation. None of the existing methods disclose how to relate a measured intra-cardiac pressure, such as the estimated pulmonary artery diastolic pressure, to the congestive heart failure patient's need for increased cardiac output. Further, none of these methods disclose how to modify the drug therapy as a function of the measured pressure to meet this need.

Examples of the above referenced existing techniques and/or devices may be found in the issued U.S. Patents listed in Table 1 below.

TABLE 1

| U.S Pat. No. | Inventor | Issue Date |
| --- | --- | --- |
| 6,155,267 | Nelson | Dec. 05, 2000 |
| 6,024,704 | Meador et al. | Feb. 15, 2000 |
| 5,810,735 | Halperin et al. | Sep. 22, 1998 |
| 5,626,623 | Kievel et al. | May 06, 1997 |
| 5,564,434 | Halperin et al. | Oct. 15, 1996 |
| 5,535,752 | Halperin et al. | Jul. 16, 1996 |
| 5,368,040 | Carney | Nov. 29, 1994 |
| 5,135,178 | Maroko | Oct. 06, 1992 |
| 4,003,379 | Ellinwood, Jr. | Jan. 18, 1977 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to treatment of congestive heart failure patients with drugs that increase cardiac output. Such problems may include, for example, the inability to monitor a congestive heart failure patient's condition, and appropriately modify the patient's drug therapy as a function of the patient's condition, in an outpatient situation. It is an object of the present invention to provide a system and method to monitor a congestive heart failure patient's condition, and appropriately modify the patient's drug therapy as a function of the patient's condition, in an outpatient situation. In particular, it is an object of the present invention to monitor a congestive heart failure patient's estimated pulmonary artery diastolic pressure and modify the patient's drug therapy as a function of the estimated pulmonary artery diastolic pressure by, for example, selecting drugs and/or adjusting dosages of drugs as a function of the estimated pulmonary artery diastolic pressure.

The present invention has certain features. In particular, various embodiments of the present invention may include a drug delivery device capable of delivering one or more drugs that increase cardiac output, at a variety of different dosages. The drug delivery device may be an implantable drug pump. Various embodiments of the present invention may also include a processor that controls the function of the drug delivery device to, for example, control which of the plurality of drugs contained within the drug delivery device are delivered and/or at what dosage the drugs are delivered.

Various embodiments of the present invention may also include a pressure sensor that detects pressure within the heart, and a pressure monitor that receives a pressure signal from the pressure sensor. In some embodiments of the invention, the pressure monitor processes the pressure signal and measures a pressure value that is generally indicative of a congestive heart failure patient's condition, and is particularly indicative of a need for increased cardiac output. Further, in some embodiments, the pressure monitor may identify a point of maximum slope on a pressure signal to, for example, estimate the pressure in the right ventricle that causes the pulmonary valve to open. In some embodiments, the measured pressure value is then used to cause the drug delivery device to adjust the drug therapy delivered by the drug delivery device by, for example, causing the drug delivery device to deliver one or more different or additional drugs and/or adjusting the dosages of the drugs delivered.

Therefore, in various embodiments of the invention, the processor that controls the operation of the drug delivery device may receive a signal that indicates the measured pressure value from the pressure monitor. In various embodiments of the invention, the processor will generate a control signal in response to the measured pressure value, to control the drug delivery device to deliver one or more different or additional drugs and/or adjust the dosages of the drugs. In some embodiments the processor may select one or more drugs or dosage levels by comparing the measured pressure value to a look-up table of pressure values and associated drugs and dosage levels. In other embodiments, the processor might select the dosages by applying one or more equations that relate pressure values to dosage. The look-up table and/or equations may be stored in memory. The look-up table and/or equations may, for example, be received via remote distribution link or RF telemetry.

In various embodiments of the invention, the processor may also receive one or more signals that indicate the patient's activity level. In various embodiments of the invention, the processor will generate the control signal in response to the measured pressure value and the patient's activity level. In some embodiments, the patient's activity level may be compared to a threshold to determine whether, considering the measured pressure value and the patient's activity, the drug therapy should be adjusted. In other embodiments, the look-up table and/or equations will relate pressure values and activity levels to dosages and/or drugs.

In some embodiments, the processor may receive programming from a physician via remote distribution link or RF telemetry. In this manner, the patient's physician may customize the drug therapy for the patient. The patient's physician may specify, for example, suitable drugs and/or dosages for particular pressures, or for pressures and activity levels. The present invention presents techniques whereby the patient's physician can relate the patient's drug therapy to the monitored pressures.

In various embodiments of the present invention, the pressure monitor and processor cooperate to continuously monitor a pressure in a patient's heart that is indicative of the patient's need for increased cardiac output, and to adjust the patient's drug therapy to meet the increased need.

The present invention has certain advantages. That is, in comparison to known implementations for treatment of congestive heart failure patients with drugs that increase cardiac output, various embodiments of the present invention may provide one or more advantages. Such advantages may include, for example, the ability to monitor a congestive heart failure patient's condition, and appropriately modify the patient's drug therapy as a function of the patient's condition, in an outpatient situation.

For example, the system and method of the present invention may use an implanted pressure monitor to monitor a congestive heart failure patient's condition, and an implanted drug delivery device to deliver the patient's drug therapy, in an outpatient situation. The system and method of the present invention can continuously determine whether there is a need for increased cardiac output by processing a pressure signal that represents pressure in the heart to measure a pressure value indicative of whether increase cardiac output is needed. Consequently, costly office visits are avoided and changes in the patient's condition between office visits are addressed. Further, by more directly measuring the symptoms of cardiac decompensation as reflected in the pressure value, the present invention more effectively treats the condition with drug therapy by increasing cardiac output. Also, the system and method of the present invention effectively increase the cardiac output as needed by selecting the appropriate drugs and/or increasing the dosage of drugs as needed.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
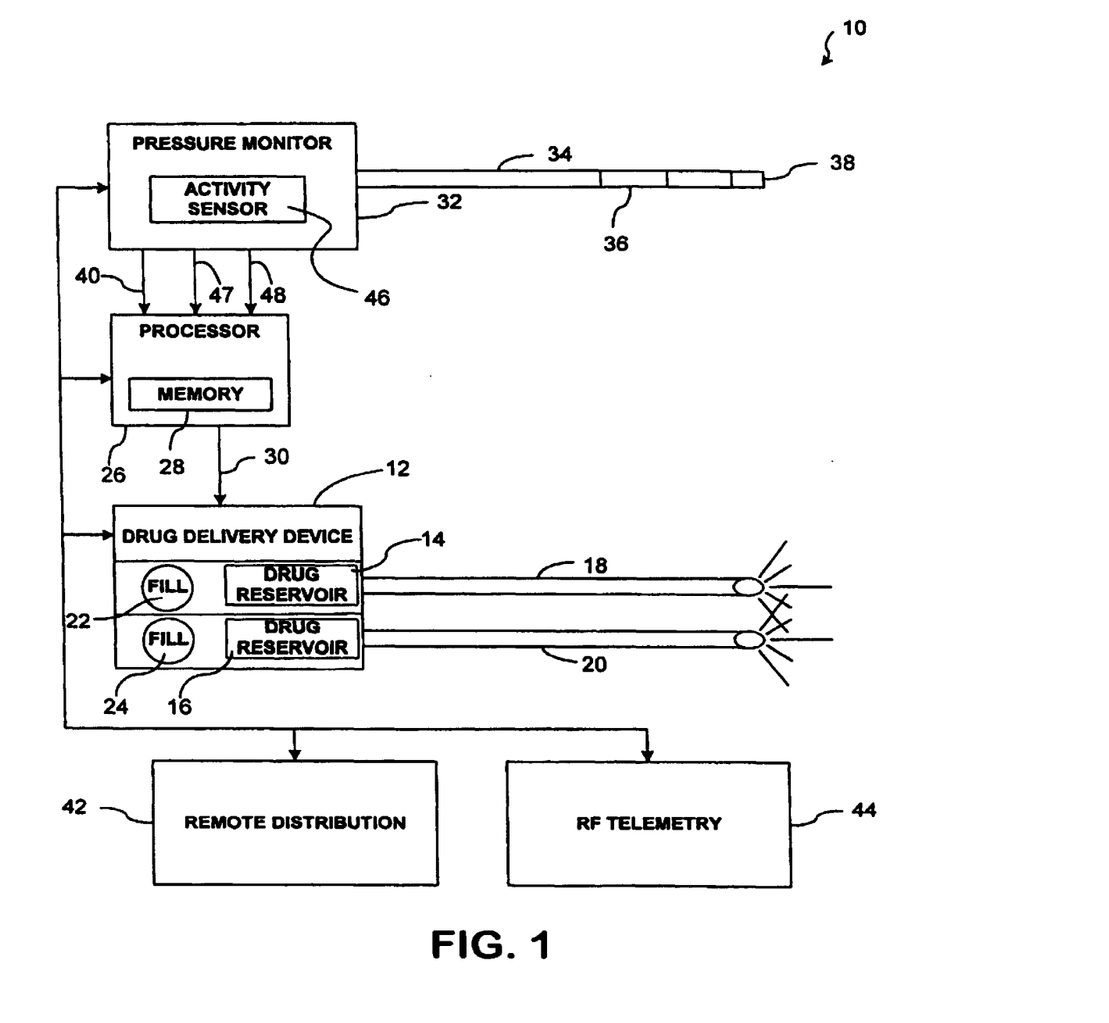
FIG. 1 is a diagram of a system including a pressure monitor and a drug delivery system.

FIG. 1 shows a system 10 illustrating an embodiment of the invention in which estimated pulmonary artery diastolic pressure is used to select drugs and/or adjust the dosage of drugs to be delivered by a drug delivery device. System 10, or any of its constituent components, could be implanted in a human being or an animal. System 10 includes drug delivery device 12, which delivers drugs to a patient. Drug delivery device 12 may include one or more reservoirs. In FIG. 1, drug delivery device 12 is shown with two reservoirs 14 and 16. Each reservoir 14, 16 may contain a drug or a mixture of drugs. Drug delivery device 12 may further include one or more fill ports 22 and 24 that assist filling or refilling of reservoirs 14 and 16.

Drug delivery device 12 may include one or more infusion apparatuses, such as catheters, that infuse drugs from reservoirs 14, 16 to infusion sites within the patient's body. FIG. 1 shows two catheters 18 and 20. Catheter 18 is shown coupled to reservoir 14 and catheter 20 is shown coupled to reservoir 16. In some embodiments of the present invention, each infusion apparatus may be coupled to more than one reservoir, or more than one infusion apparatus may be coupled to each reservoir. Drug delivery device 12 also may include one or more pumps (not shown) that deliver drugs from the reservoirs to the infusion apparatuses.

The infusion site may depend upon the drug being infused. Each of catheters 18 and 20 may dispense drugs at one or more infusion sites within the patient's body. For example, a catheter may deliver drugs to the patient's subclavian vein, superior vena cava, or to the patient's fatty tissue. If the patient has more than one catheter, the catheters need not deliver drugs to the same infusion site.

The drugs being delivered may be delivered by a constant drip, a periodic bolus, a combination of these methods, or some other delivery method. The present invention is not limited to a particular drug delivery method.

Drug delivery device 12 may be an implantable drug pump. Examples of implantable drug pumps include a number of SynchroMed™ pumps manufactured by and commercially available from Medtronic Inc. of Minneapolis, Minn. Pumps of this kind typically include self-sealing reservoirs that may be refilled by a needle and syringe, and need not be surgically removed when empty. The needle and syringe may also be used to drain a pump of one drug, flush the reservoir, and refilled the reservoir with a different drug. The invention is not limited to use with SynchroMed pumps, however, and may be adapted for use with other drug delivery devices.

System 10 also includes a processor 26 that controls the operation of drug delivery device 12. By controlling the operation of drug delivery device 12, processor 26 controls the drug therapy delivered to the patient at any given time. Processor 26 may, for example, control which drugs are delivered by the drug delivery device 12, by controlling which pumps are active. Processor 26 may also control the dosage of the drugs delivered by drug delivery device 12 by controlling the activity of the pumps. Processor 26 may control the operation of drug delivery device 12 via control signal 30.

The present invention presents techniques for selecting a drug therapy based on the pressure of the blood flowing inside the patient's heart. System 10, as shown in FIG. 1, includes pressure monitor 32, which is coupled to pressure sensor 36 by lead 34. An example of pressure monitor 32 that may be used with this embodiment of the present invention is the Chronicle™ Implantable Hemodynamic Monitor manufactured by and commercially available from Medtronic, Inc. of Minneapolis, Minn. As will be described below, pressure monitor 32 may measure the estimated pulmonary artery diastolic pressure (ePAD) as a function of the pressure signals received from pressure sensor 36.

Pressure sensor 36 responds to the absolute pressure inside the patient's heart. Pressure sensor 36 may be one of many forms of pressure sensors. One form of pressure sensor that is useful for measuring blood pressure inside a human heart is a capacitive absolute pressure sensor, as described in U.S. Pat. No. 5,564,434 to Halperin, et al., hereby incorporated by reference herein in its entirety. Pressure sensor 36 may also be a piezoelectric crystal or piezoresistive pressure transducer. The invention is not limited to any particular kind of pressure sensor.

Pressure monitor 32 is also coupled to electrode 38 located at the distal end of lead 34 near pressure sensor 36. Electrode 38 senses the electrical activity in the heart. Pressure monitor 32 can sense R-waves via electrode 38.

The pressure monitor 32 may also include an activity sensor 46, which may be a piezoceramic accelerometer bonded to a hybrid circuit. Activity sensor 46 typically, although not necessarily, provides a sensor output that varies as a function of a measured parameter relating to the patient's metabolic requirements or activity level. Furthermore, pressure monitor 32 may calculate a heart rate as a function of R—R intervals collected via R-wave sensing. Based on the output of activity sensor 46 and/or the calculated heart rate, it may be determined if the patient is at rest, as indicated by minimal activity sensor output, or performing activities, as indicated by significant activity sensor output and elevated heart rates.

As shown in FIG. 1, processor 26 receives a signal 40 from pressure monitor 32. Signal 40 may indicate the ePAD as measured by the pressure monitor 32. Processor 26 may select a drug therapy as a function of signal 40. Processor 26 may select one or more drugs from a plurality of drugs contained in drug delivery device 12 as a function of signal 40, and may control the drug delivery device to deliver the selected drug or drugs. Processor 26 may select a dosage for one or more drugs delivered by drug delivery device 12, and may control the drug delivery device 12 to deliver the each of the drugs at the selected dosage. In some embodiments of the present invention, processor 26 may perform both the drug selection function and the dosage selection function.

When signal 40 indicates an estimated pulmonary artery diastolic pressure value, processor 26 may select the drugs and/or dosages by comparing the ePAD value indicated by signal 40 to a look-up table of ePAD values and associated drugs and/or dosages. As an alternative, processor 26 may select the dosages for each of the one or more drugs to be delivered by applying equations that relate ePAD values to dosages. The look-up table or equations may be stored in memory 28. The look-up table or equations may, for example, be received via remote distribution link 42, RF telemetry 44, or from an external programmer.

Processor 26 may also receive an activity sensor output 47, which pressure monitor 32 generates from activity sensor 46, and a signal 48, which is indicative of the patient's heart rate, from pressure monitor 32. Heart rate signal 48 may reflect R-waves sensed by pressure monitor 32, in which case processor 26 may calculate the heart rate as a function of signal 48. Alternatively, signal 48 may, if pressure monitor 32 itself calculates the heart rate from sensed R-waves, reflect the patient's heart rate. In either case, processor 26 determines the patient's activity level as a function of the activity sensor output 47 and/or the heart rate.

In such an embodiment, processor 26 may select one or more drugs to be delivered by drug delivery device 12 from a plurality of drugs contained in drug delivery device 12 as a function of pressure signal 40 and the determined activity level. In addition or in the alternative, processor 26 may select a dosage for one or more drugs to be delivered by drug delivery device 12 as a function of pressure signal 40 and the determined activity level. In some embodiments of the present invention, the activity level may be implemented as a threshold. For example, if the activity sensor output 47 and/or the heart rate exceed a threshold value, the processor may disregard an elevated ePAD and control drug delivery device 12 to deliver the same drugs at the same dosages. In other embodiments, processor 26 may select the drugs and/or dosages by comparing the ePAD value indicated by signal 40, activity sensor output 47, and the heart rate to a look-up table that maps ePAD values, activity sensor output values, and heart rate values to associated drugs and/or dosages. In an alternative embodiment, processor 26 may select the dosages for each of the one or more drugs to be delivered by applying equations that relate ePAD values, activity sensor output values, and heart rates to dosages. The threshold values, look-up table or equations may be stored in memory 28. The threshold values, look-up table or equations may, for example, be received via remote distribution link 42, RF telemetry 44, or from an external programmer.

Although shown in FIG. 1 as logically separate from pressure monitor 32 and drug delivery device 12, processor 26 may be housed inside pressure monitor 32, or inside drug delivery device 12. Alternatively, processor 26 may be separate from both pressure monitor 32 and drug delivery device 12. Further, pressure monitor 32, drug delivery device 12 and processor 26 may be realized as a single implantable device.

Processor 26 may be implemented as a microprocessor, for example, or as an ASIC, FPGA, discrete logic circuitry, or analog circuitry. Processor 26 may execute instructions stored in memory 28, which may comprise any computer-readable medium suitable for storing instructions, including random access memory (RAM), read-only memory (ROM) non-volatile random access memory (NVRAM), electrically erasable programmable read-only memory (EEPROM), flash memory, and the like.

Figure 2:
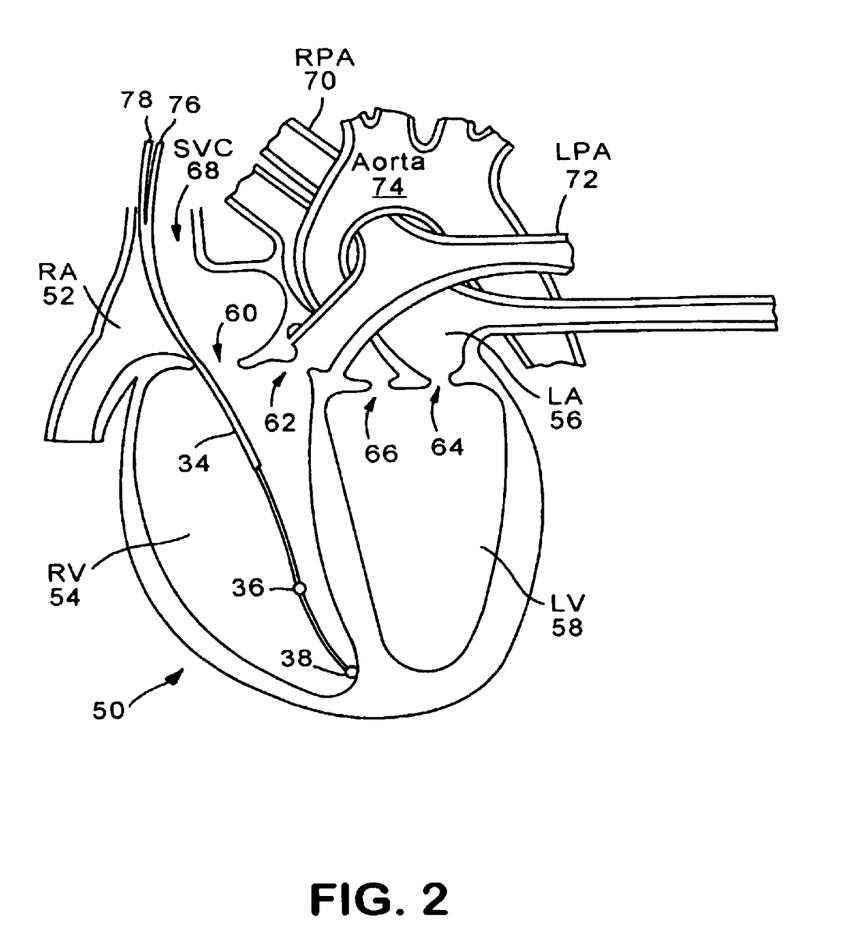
FIG. 2 is a diagram of a human heart, with a pressure sensor and a lead.

FIG. 2 is a diagram of a human heart 50, including a pressure sensor 36, electrode 38 and a lead 34. Pressure sensor 36 and electrode 38 may, as shown in FIG. 2, be placed inside right ventricle 54 of heart 50. Sensor 36 is coupled to lead 34, which extends from right ventricle 54, through right atrioventricular valve 60, and through superior vena cava 68. Lead 34 extends further through the patient's circulatory system, eventually exiting the circulatory system and coupling to implanted pressure monitor 32 (not shown in FIG. 2). Pressure monitor 32 may, for example, be implanted in the patient's abdomen or upper chest.

Sensor 36 may generate pressure signals itself or may modulate pressure signals conducted through lead 34 along wires 76 and 78. The pressure signals are a function of the fluid pressure in right ventricle 54. Pressure monitor 32 receives, monitors and analyzes the pressure signals, as will be described in more detail below.

In systole, right ventricle 54 and left ventricle 58 contract. For a brief period, no blood leaves ventricles 54 and 58, and the contraction is isovolumetric. During isovolumetric contraction, right atrioventricular valve 60 and left atrioventricular valve 64 are closed by backward pressure differential forces. Aortic valve 66 and pulmonary valve 62 are likewise closed, as the pressure in ventricles 54 and 58 is insufficient to force blood through them.

Consequently, isovolumetric contraction causes the blood in ventricles 54 and 58 to undergo increasing pressure. In a short time, the pressure in right ventricle 54 overcomes the pressure in pulmonary arteries 70 and 72, drives pulmonary valve 62 open, and ejects blood from right ventricle 54 into pulmonary arteries 70 and 72. Similarly, the pressure in left ventricle 58 overcomes the pressure in aorta 74, driving open aortic valve 66 and ejecting blood into aorta 74. The pressure needed to open aortic valve 66 is normally much higher than the pressure needed to open pulmonary valve 62.

The pressure needed to open pulmonary valve 62 is, for practical purposes, an accurate measure of the pulmonary artery diastolic pressure (PAD), and is referred to as the estimated pulmonary artery diastolic pressure or ePAD. ePAD is a significant pressure in patient monitoring. In particular, ePAD reflects the condition of a congestive heart failure patient.

ePAD is a significant pressure because ePAD closely reflects the pulmonary capillary wedge pressure, or PCWP, which reflects the average pressure in left atrium 56 over a cardiac cycle, also called the mean left atrial pressure or mean LAP. In addition, ePAD reflects the filling pressure in left ventricle 58 during diastole, also called the left ventricular end diastolic pressure or LVEDP. In a healthy heart, LAP and LVEDP range from approximately 8 mmHg to 12 mmHg. ePAD may be somewhat higher than LAP and LVEDP, but past studies indicate a strong correlation between ePAD, PCWP, mean LAP and LVEDP. In a heart having congestive heart failure, each of these pressures may be considerably elevated, as will be discussed below.

Mean LAP and LVEDP are pressures on the left side of heart 50. Practical considerations make it difficult to measure pressures on the left side of heart 50 directly. These pressures may be measured indirectly, however, by placing sensor 36 in right ventricle 54 and measuring ePAD with pressure monitor 32.

Measurement of ePAD is not equivalent to measuring the highest pressure in right ventricle 54. During isovolumetric contraction in systole, the pressure in right ventricle 54 increases and forces pulmonary valve 62 open. Pressure in right ventricle 54 does not peak at this point, however. Rather, pressure in right ventricle 54 increases during ejection as well, but the pressure increases at a reduced rate.

Figure 3:
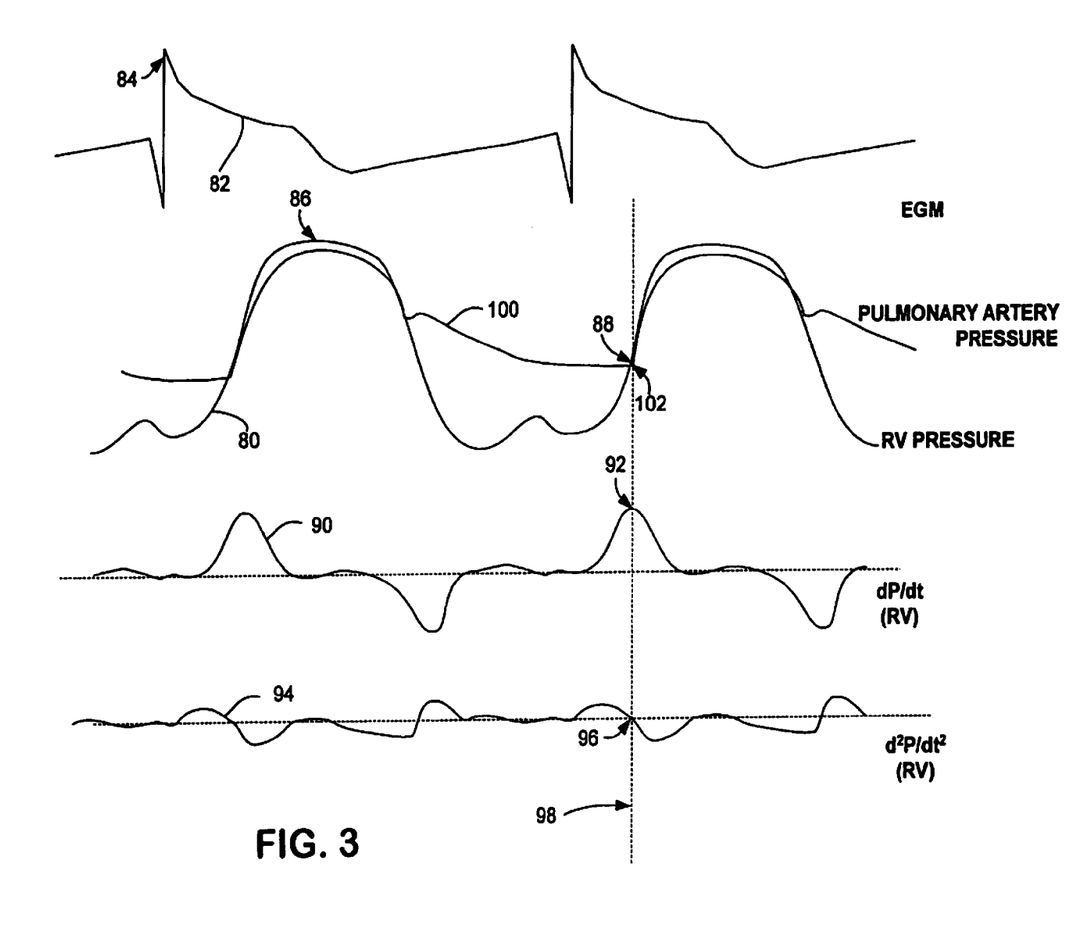
FIG. 3 is a timing diagram showing a ventricular electrogram signal, a signal indicative of right ventricular pressure, and the first and second derivatives of the right ventricular pressure signal.

It is this change in the rate of increase of pressure that helps identify ePAD, as illustrated in FIG. 3. Pressure signal 80 from sensor 36 in right ventricle 54 is shown in reference to ventricular electrogram (EGM) signal 82. EGM signal 82 may be sensed by electrode 38.

R-wave 84 in EGM signal 82 represents ventricular depolarization of heart 50. Following ventricular depolarization, pressure in right ventricle 54 increases, eventually reaching a peak pressure at 86.

When the pressure in right ventricle 54 overcomes the pressure in pulmonary arteries 70 and 72, pulmonary valve 62 is driven open. When pulmonary valve 62 opens, contraction is no longer isovolumetric. Pressure in right ventricle 54, although still increasing due to ventricular contraction, increases at a slower rate. As a result, there is an inflection point 88 in pressure signal 80 when pulmonary valve 62 opens.

ePAD may be found by determining the pressure at the point on right ventricular pressure curve 80 corresponding to the inflection point 88. Inflection point 88 may be found by taking the first derivative of right ventricular pressure with respect to time, or dP/dt. Because the slope of pressure signal 80 is at its maximum at inflection point 88, the peak 92 of dP/dt signal 90 corresponds to inflection point 88. Therefore, ePAD may be found by finding the point on right ventricular pressure signal 80 corresponding to the maximum value of dP/dt. Inflection point 88 may also be found by taking the second derivative of right ventricular pressure with respect to time, or $d^2P/dt^2$. In this case, ePAD is the pressure at the point on right ventricular pressure signal 80 corresponding to the point 96 at which signal 94 of $d^2P/dt^2$ goes negative for the first time after R-wave 84. The time at which inflection point 88, peak 92 and zero crossing 96 occur is indicated by reference line 98.

Pressure monitor 32 may include differentiating circuits that generate $d^2P/dt^2$ signal 94 and/or dP/dt signal 90. Pressure monitor 32 may further include circuits to detect when $d^2P/dt^2$ signal 94 crosses zero in the negative direction after the R-wave, or when dP/dt signal 90 peaks, both of which occur at time 98. By detecting when inflection point 88 occurs, pressure monitor 32 may measure the pressure 102 in right ventricle 54 at inflection point 88, which is ePAD.

FIG. 3 also shows an exemplary pulmonary artery pressure curve 100 superimposed on right ventricle pressure signal 80. As shown in FIG. 3, the point 102 at which pulmonary artery pressure is nearly equal to the right ventricle pressure is at inflection point 88, when signal 80 and curve 100 cross each other. The pressure at inflection point 88 is ePAD, the pressure at which the pressure in right ventricle 54 overcomes the pressure in pulmonary arteries 70 and 72, opening pulmonary valve 62. It has been verified by experimentation that ePAD is a close estimation of PAD.

As mentioned above, patients having chronic congestive heart failure often exhibit elevated ePAD levels. This is because the hearts of patients having congestive heart failure may fail to achieve adequate circulation to their organs and tissues, a condition known as cardiac decompensation. As a result of the inability to achieve adequate forward circulation, the hearts of congestive heart failure patients may also fail to adequately expel the blood that is being returned to them from the organs and tissues. When blood is unable to return to the heart from the pulmonary system, the blood dams up in the lungs, and pulmonary edema results.

The damming of the blood in the lungs leads to increased pressure in the pulmonary circulatory system, which results in an elevated pulmonary artery pressure. Elevated pulmonary artery pressure is therefore an indication of the condition of a congestive heart failure patient, and a sign of risk of pulmonary edema.

Because ePAD is a close approximation of pulmonary artery pressure, elevated ePAD is also an indication of the congestive heart failure patient's condition, and a sign of risk of pulmonary edema. In general, as a patient's ePAD approaches approximately 25 mmHg, the patient's risk of pulmonary edema increases. When a patient's ePAD exceeds 25 mmHg, pulmonary edema is very likely to occur.

Cardiac decompensation and pulmonary edema can be serious. In many cases, the conditions require intensive care and hospitalization. Cardiac decompensation and pulmonary edema can be fatal.

Causing more blood to be expelled from the heart, i.e., increasing cardiac output would increase the inadequate forward flow of blood to the organs and reduce the damming of blood in the lungs caused by cardiac decompensation. Therefore, therapies to treat congestive heart failure patients may include therapies to increase cardiac output.

Cardiac output (CO) is defined as the volume of blood pumped by each ventricle per minute. CO is determined by two factors: heart rate (HR) in units of beats per minute, and stroke volume (SV) in units of volume of blood pumped per stroke, i.e., per beat. The relationship between CO, HR and SV is usually expressed:

$CO = HR \times SV$

One way to increase CO is to increase SV, i.e., cause the ventricles to pump more blood per beat. One way to cause the ventricles to pump more blood per beat is administer a drug with a positive inotropic effect on the heart. A drug with a positive inotropic effect on the heart increases the heart's contractility, i.e. causes the heart to beat more forcefully, thereby ejecting more blood volume per stroke. Drugs that have a positive inotropic effect on the heart include cardiac glycosides such as digitalis, digoxin and digitoxin, beta-adrenergic agonists such as dopamine and dobutamine, and phosphodiesterase inhibitors such as amrinone and milrinone.

Because elevated ePAD reflects the damming of blood in the lungs, which is a symptom of congestive heart failure, ePAD may also reflect the need for increased cardiac output to overcome cardiac decompensation. Consequently, ePAD reflects the need for a therapy to increase the cardiac output. Thus, ePAD may, for example, reflect the need to change from one of the drugs listed above to another more potent drug or combination of drugs listed above. ePAD may also reflect the need to increase or decrease the dosage of one or more of the drugs listed above. The present invention is not limited to the listed drugs or classes of drugs, but is instead intended to include use of any drug to increase cardiac output.

Figure 4:
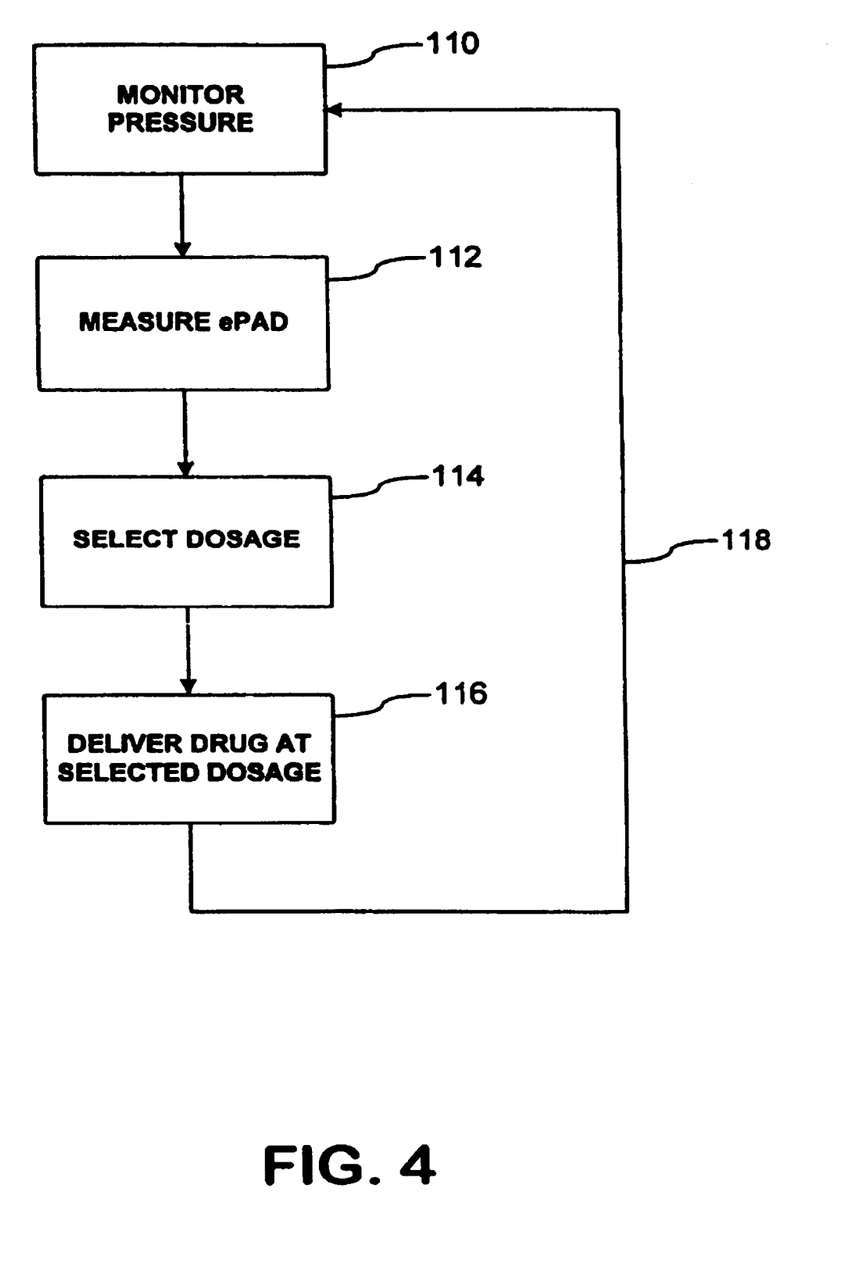
FIG. 4 is a flow diagram illustrating additional techniques of the invention.

Techniques for ePAD-based adjustment of the dosage of a drug that increases cardiac output are shown in FIG. 4. Pressure monitor 32 monitors pressure in the right ventricle 54 of the heart 50 via pressure sensor 36 coupled to lead 34 (110). Pressure monitor 32 also processes the pressure signal that it receives from pressure sensor 36 to measure the estimated pulmonary artery diastolic pressure (112). Pressure monitor 32 may, for example, identify the pressure value at the point of maximum slope in the pressure signal by either of the techniques described above. Pressure monitor 32 generates a pressure signal 40 as a function of the measured ePAD, which is received by processor 26.

Processor 26 selects a dosage for each of the one or more drugs to be delivered by drug delivery device 12 as a function of pressure signal 40 (114) and generates control signal 30, which is received by drug delivery device 12. Drug delivery device 12 delivers each of the one or more drugs to the patient at the selected dosage as a function of control signal 30 (116) by, for example, increasing or decreasing the rate of one or more of its drug pumps. If pressure monitor 32 detects an elevated ePAD, for example, processor 26 may generate control signal 30 to cause drug delivery device 12 to increase the dosage of the one or more drugs that are delivered to the patient.

Increasing the dosage of the one or more drugs delivered by drug delivery device 12 may increase the cardiac output. The results of increasing the cardiac output may be reflected in the measured ePAD, which may be used to further adjust dosage of the drug delivered by drug delivery device 12. Thus, system 10 may use feedback continually to monitor ePAD and adjust the dosage of one or more drugs delivered to the patient as a function of the ePAD (118).

Figure 5:
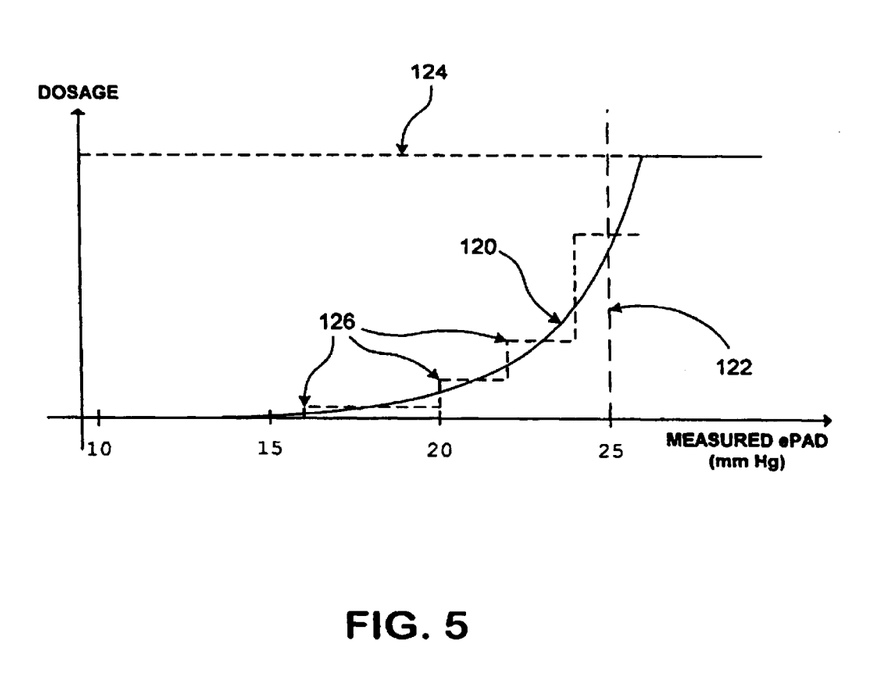
FIG. 5 is a graph showing exemplary drug dosages as a function of estimated pulmonary artery diastolic pressure.

FIG. 5 is a graph illustrating an exemplary relationship between ePAD and dosage. Curve 120 defines the appropriate dosage as a function of the patient's calculated ePAD. Curve 120 may be defined by an equation that applies over a range of ePAD values, the equation being of the general form dosage=f(ePAD).

As shown in FIG. 5, the dosage increases non-linearly as the patient's ePAD approaches 25 mmHg (122). The increase in slope of curve 120 represents a rapid increase in dosage when the patient is at risk of pulmonary edema up to the maximum dosage 124 for the particular drug. The rapid increase causes SV to rise, consequently boosting CO, thereby alleviating the damming in the pulmonary circulation, reducing the pulmonary artery pressure, and reducing the risk of pulmonary edema. Although curve 120 defines dosages corresponding to an ePAD of about 14 mmHg or greater, the present invention contemplates the definition of dosages over any range of ePAD values.

The dosage is limited to the patient's safe maximum dosage 124. Therefore, programming the device above a safe dosage limit is not possible. This maximum level is tailored to the patient and chosen by the physician.

The relationship between ePAD and dosage may also be described by discrete dosages for discrete ePAD values or ranges of ePAD values. FIG. 5 shows one such correlation between discrete ePAD values and discrete dosages, resulting in a piecewise linear relationship 126. The subset of ePAD values between 20 mmHg and 22 mmHg, for example, corresponds to a single dosage. Similarly, other subsets of ePAD values correspond to single dosages.

Figure 6:
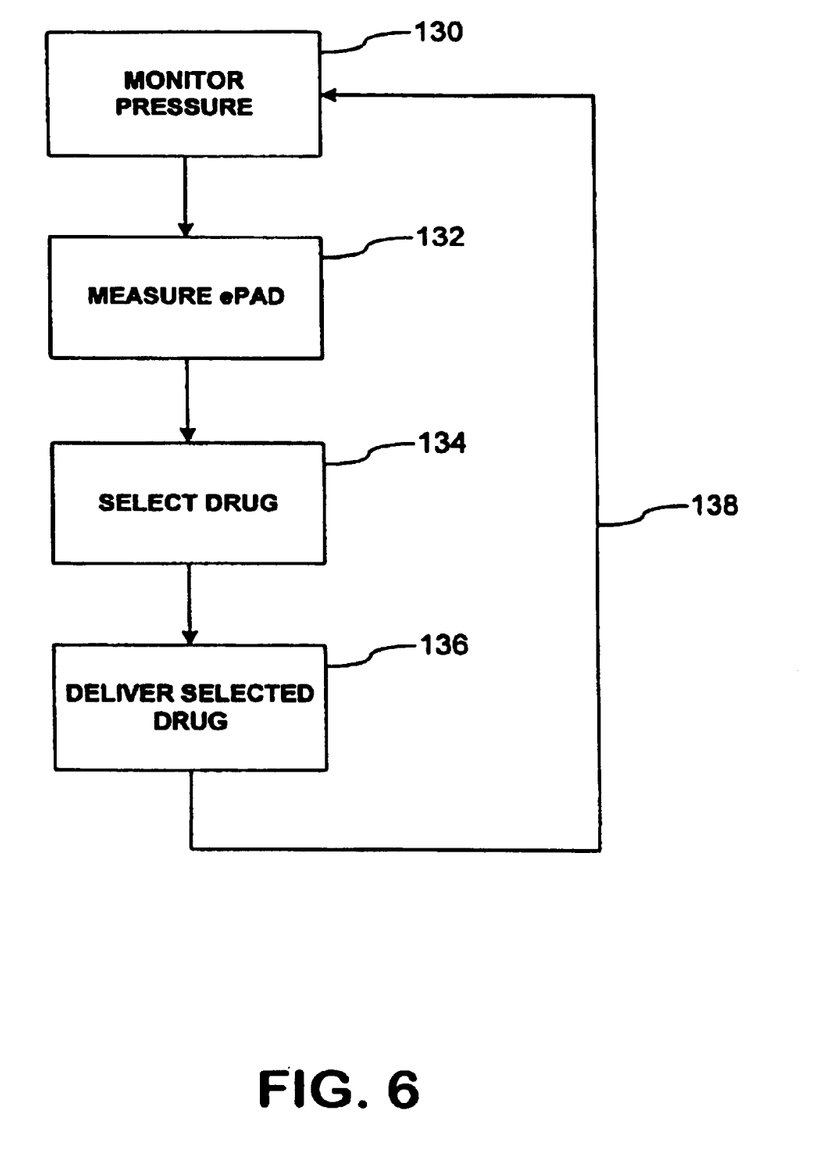
FIG. 6 is a flow diagram illustrating techniques of the invention.

Techniques for ePAD-based selection of one or more drugs from a plurality of drugs that increase cardiac output are shown in FIG. 6. Pressure monitor 32 monitors pressure in the right ventricle 54 of the heart 50 via pressure sensor 36 coupled to lead 34 (130). Pressure monitor 32 also processes the pressure signal that it receives from pressure sensor 36 to measure the estimated pulmonary artery diastolic pressure (132). Pressure monitor 32 may, for example, identify the pressure value at the point of maximum slope in the pressure signal by either of the techniques described above. Pressure monitor 32 generates a pressure signal 40 as a function of the measured ePAD, which is received by processor 26.

Processor 26 selects one or more drugs to be delivered by drug delivery device 12 from a plurality of drugs contained in drug delivery device 12 as a function of pressure signal 40 (134) and generates control signal 30, which is received by drug delivery device 12. Drug delivery device 12 delivers the one or more selected drugs to the patient as a function of control signal 30 (136) by, for example, activating the one or more drug pumps associated with the reservoirs that contain the selected drugs. For example, if the ePAD value measured by pressure monitor 32 and delivered to processor 26 via pressure signal 40 indicates that the drug contained in reservoir 14 should be delivered to the patient, processor 26 will select that drug and send control signal 30 to drug delivery device 12 to cause drug delivery device 12 to activate the pump associated with reservoir 14.

Changing the delivered drug or delivering additional drugs may increase the cardiac output. The results of increasing the cardiac output may be reflected in the measured ePAD, which may be used to make further changes to the roster of drugs delivered by drug delivery device 12. Thus, system 10 may use feedback continually to monitor ePAD and select the appropriate one or more drugs to be delivered to the patient as a function of the ePAD (138).

Figure 7:
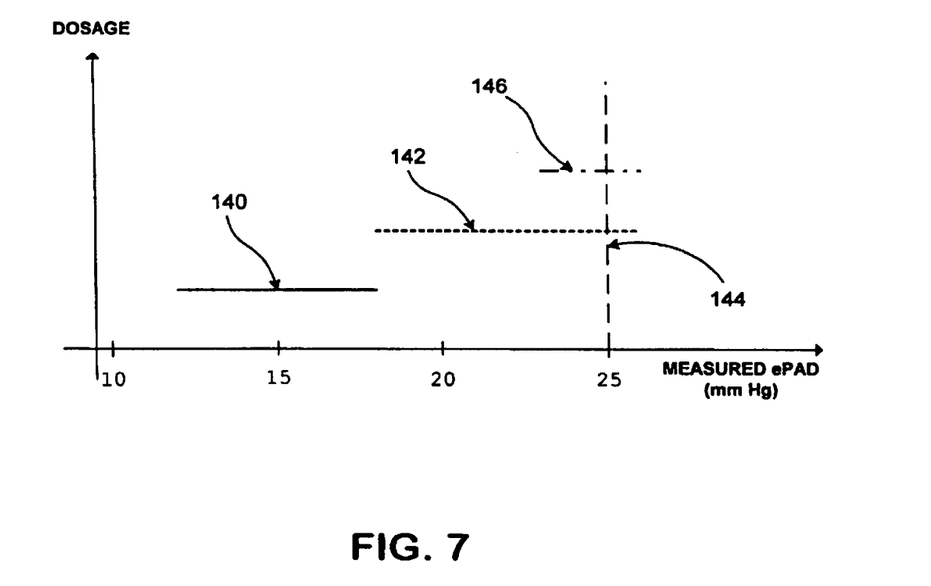
FIG. 7 is a graph showing the selection of a drug as a function of estimated pulmonary artery diastolic pressure.

FIG. 7 is a graph illustrating an exemplary relationship between ePAD and drug selection. Between 12 mmHg and 18 mmHg, drug 140 of a first effectiveness with respect to increasing cardiac output is delivered at a constant dosage. In this example, at 18 mmHg the need for increased cardiac output has exceeded the effectiveness of drug 140. Delivery of drug 140 ceases in favor of delivery of drug 142 at a higher dosage, which has a higher effectiveness with respect to increasing cardiac output. As the patient's measured ePAD approaches 25 mmHg (144) and pulmonary edema is eminent, supplemental drug 146 is delivered in addition to drug 142 in a further effort to increase cardiac output.

Figure 8:
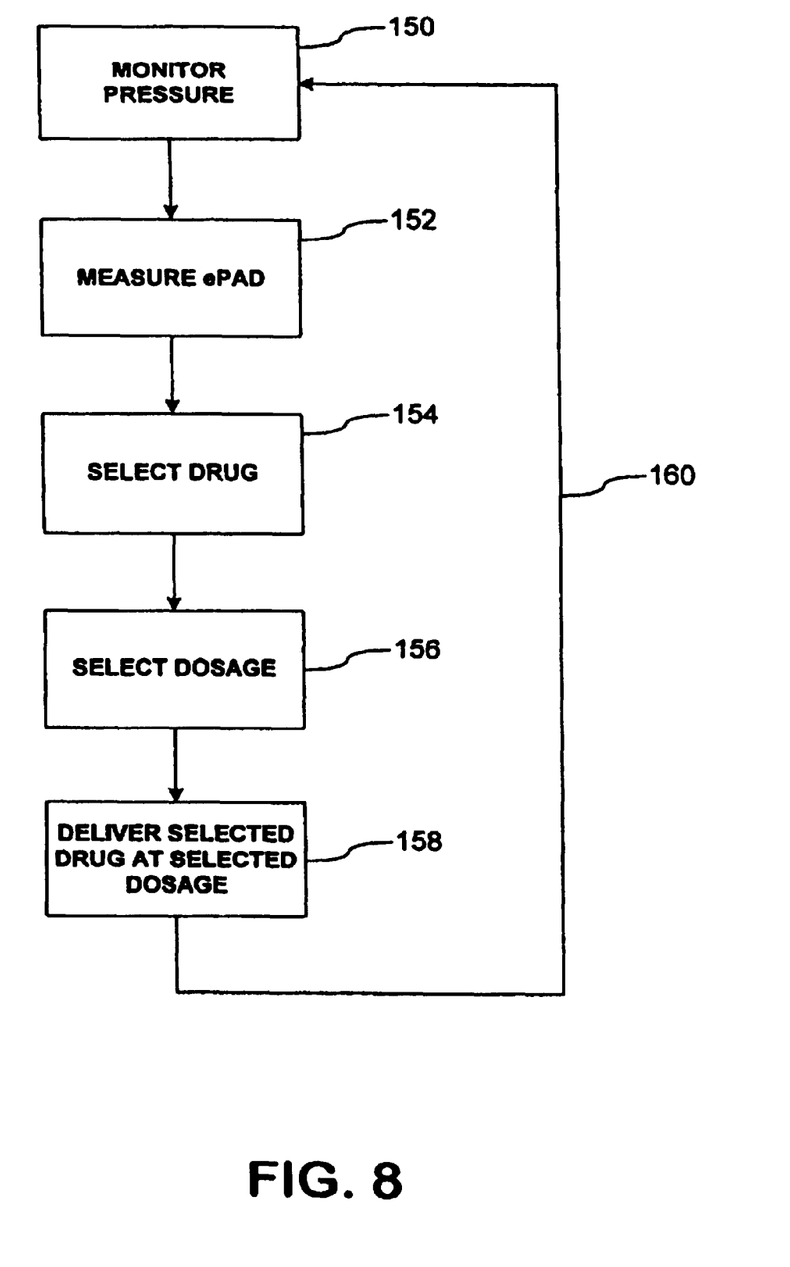
FIG. 8 is a flow diagram illustrating techniques of the invention, generally combining the techniques shown in FIGS. 4 and 6.

A combined technique for ePAD-based adjustment to drug therapy, combining the techniques for ePAD-based selection of one or more drugs from a plurality of drugs and ePAD-based adjustment of the dosage of one or more drugs, is shown in FIG. 8. Pressure monitor 32 monitors pressure in the right ventricle 54 of the heart 50 via pressure sensor 36 coupled to lead 34 (150). Pressure monitor 32 also processes the pressure signal that it receives from pressure sensor 36 to measure the estimated pulmonary artery diastolic pressure (152). Pressure monitor 32 may, for example, identify the pressure value at the point of maximum slope in the pressure signal by either of the techniques described above. Pressure monitor 32 generates a pressure signal 40 as a function of the measured ePAD, which is received by processor 26.

Processor 26 selects one or more drugs to be delivered by drug delivery device 12 from a plurality of drugs contained in drug delivery device 12 as a function of pressure signal 40 (154), selects a dosage for each of the one or more selected drugs as a function of pressure signal 40 (156), and generates control signal 30, which is received by drug delivery device 12. Drug delivery device 12 delivers each of the one or more selected drugs to the patient at the selected dosage as a function of control signal 30 (158) as described above. Furthermore, as described above the results of adjusting the drug therapy may be reflected in the measured ePAD, which may be used to further adjust the drug therapy. Thus, system 10 may use feedback continually to monitor ePAD and select drugs and adjust dosages as a function of the ePAD (160).

Figure 9:
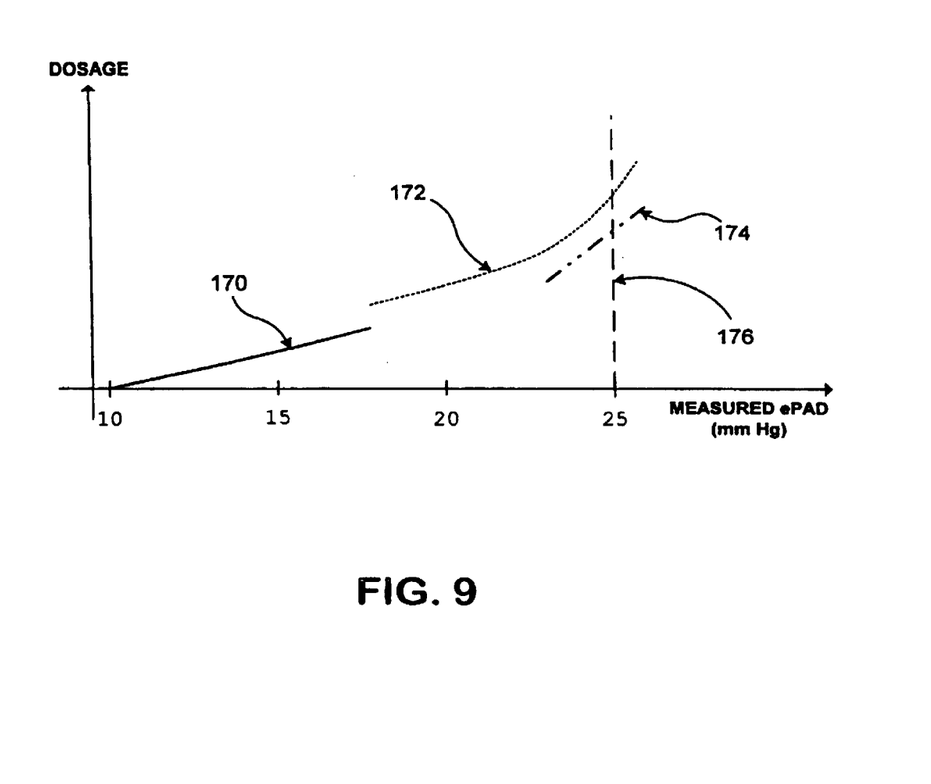
FIG. 9 is a graph showing the selection and dosages of drugs as a function of estimated pulmonary artery diastolic pressure.

FIG. 9 is a graph illustrating an exemplary relationship between ePAD and a drug therapy that includes three drug options 170, 172 and 174. The curve for each of the drugs 170, 172 and 174 defines the appropriate dosage as a function of the patient's calculated ePAD. Each curve may be defined by an equation that applies over a range of ePAD values, the equation being of the general form dosage=f (ePAD). The relationship between ePAD and dosage for each of the drugs 170, 172 and 174 may also be described by discrete dosages for discrete ePAD values or ranges of ePAD values as described with reference to FIG. 5.

As shown in FIG. 9, between 10 mmHg and 18 mmHg, drug 170 of a first effectiveness with respect to increasing cardiac output is delivered. Drug 170 is delivered in a linearly increasing fashion to meet the increased need for cardiac output evidenced by the increased measured ePAD values throughout this range. In this example, at 18 mmHg the need for increased cardiac output has exceeded the effectiveness of drug 170. Delivery of drug 170 ceases in favor of delivery of drug 172, which has a higher effectiveness with respect to increasing cardiac output. Between 18 mmHg and 23 mmHg, drug 172 is also delivered in a roughly linearly increasing fashion to meet the increased need for cardiac output. As the patient's measured ePAD approaches 25 mmHg (176) and pulmonary edema is eminent, the dosage of drug 172 increases non-linearly and supplemental drug 174 is delivered in addition to drug 172 in a further effort to increase cardiac output. The rapid increase in the dosage of drug 172 and the addition of supplemental drug 174 cause SV to rise, consequently boosting CO, thereby alleviating the damming in the pulmonary circulation, reducing the pulmonary artery pressure, and reducing the risk of pulmonary edema.

During periods of exercise, the ePAD can increase significantly as the loading conditions to the left side of the patient's heart increase. An increase in ePAD caused by the patient's increased activity might not indicate a change in the patient's condition or a need for increased cardiac output. Therefore it may be desirable to consider the patient's activity level in addition to the measured ePAD when determining whether to adjust the drug therapy.

Figure 10:
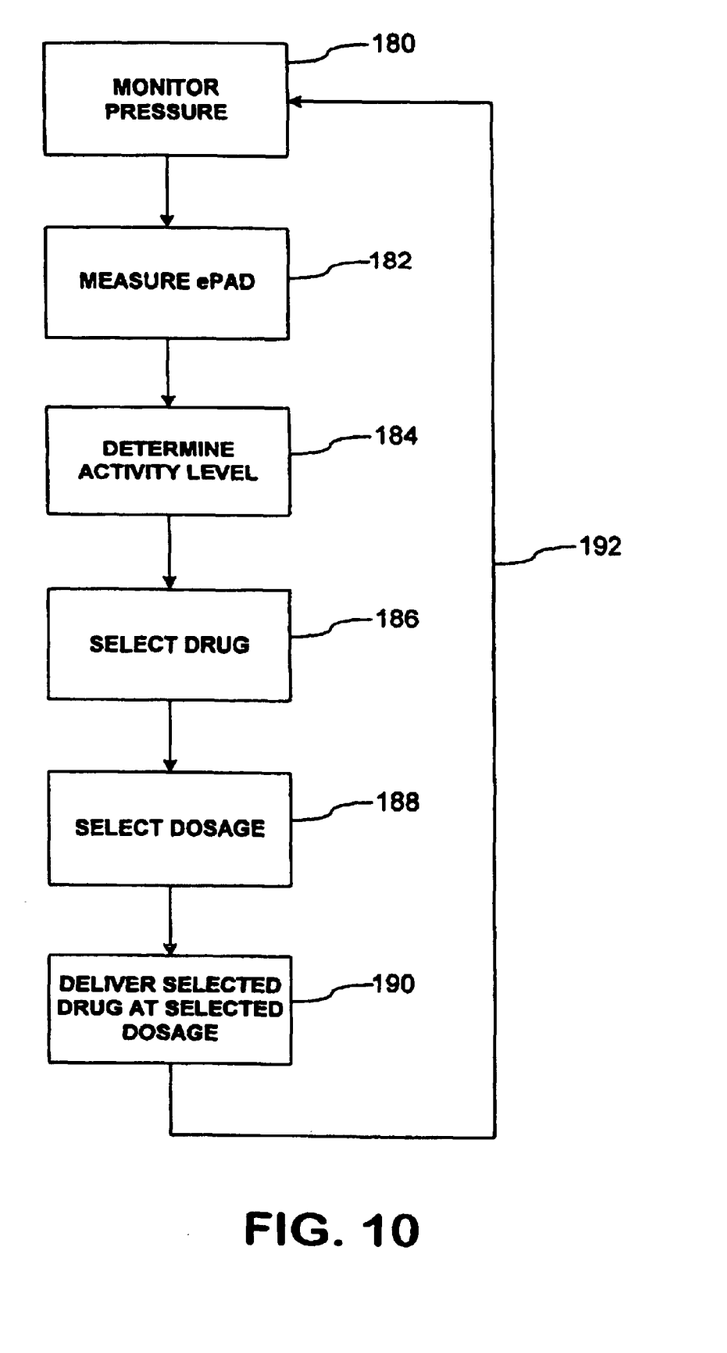
FIG. 10 is a flow diagram illustrating techniques of the invention, generally combining the techniques shown in FIGS. 4 and 6, further taking into consideration the activity level of the patient.

A further technique for ePAD-based adjustment to drug therapy, combining the techniques described above with a consideration of the patient's activity level, is shown in FIG. 10. Pressure monitor 32 monitors pressure in the right ventricle 54 of the heart 50 via pressure sensor 36 coupled to lead 34 (180). Pressure monitor 32 also processes the pressure signal received from pressure sensor 36 to measure the estimated pulmonary artery diastolic pressure (182). Pressure monitor 32 may, for example, identify the pressure value at the point of maximum slope in the pressure signal by either of the techniques described above. Pressure monitor 32 generates a pressure signal 40 as a function of the measured ePAD, which is received by processor 26.

Processor 26 also receives an activity sensor output 47, which pressure monitor 32 generates from activity sensor 46, and a signal 48, which is indicative of the patient's heart rate, from pressure monitor 32. Heart rate signal 48 may reflect R-waves sensed by pressure monitor 32, in which case processor 26 may calculate the heart rate as a function of signal 48. Alternatively, signal 48 may, if pressure monitor 32 itself calculates the heart rate from sensed R-waves, reflect the patient's heart rate. In either case, processor 26 determines the patient's activity level as a function of the activity sensor output 47 and/or the heart rate (184).

Processor 26 selects one or more drugs to be delivered by drug delivery device 12 from a plurality of drugs contained in drug delivery device 12 as a function of pressure signal 40 and the determined activity level (186), selects a dosage for each of the one or more selected drugs as a function of pressure signal 40 and the determined activity level (188), and generates control signal 30, which is received by drug delivery device 12. In some embodiments of the present invention, when processor 26 receives an elevated ePAD from pressure monitor 32 and also determines an increased activity level as a function of activity sensor output 47 and signal 48, processor 26 may determine that no ePAD-based change to the drugs or dosages should be made. If, on the other hand, processor 26 receives an elevated ePAD in the absence of an increased activity level, processor 26 may select the drugs and dosages indicated by the elevated ePAD.

Drug delivery device 12 delivers each of the one or more selected drugs to the patient at the selected dosage as a function of control signal 30 (190) as described above. Furthermore, as described above, the results of adjusting the drug therapy may be reflected in the measured ePAD, which may be used to further adjust the drug therapy. Thus, system 10 may use feedback continually to monitor ePAD, determine the patient's activity level, and select drugs and adjust dosages as a function of the ePAD and the determined activity level (192).

Because pressure monitor 32 can measure ePAD during each cardiac cycle, drugs may be selected and the dosage of the drugs may be adjusted as often as on a beat-to-beat basis. The present invention is not however, limited to beat-to-beat drug and dosage adjustment. Nor is the present invention limited to measuring ePAD each cardiac cycle. Nor is the present invention limited to selecting drugs and adjusting dosages on the basis of a single ePAD measurement. ePAD may be measured and drugs and dosage may be selected at any frequency or on any basis. The drugs and dosages may, for example, be selected periodically, where the period between selections is longer than the period between ePAD measurements. For example, in some embodiments of the present invention, the drugs and dosage may be selected on the basis of the average of the ePAD values measured during the period between selections.

Input/output devices 42 and 44 allow a person, such as the patient's physician, to exchange information with processor 26, pressure monitor 32 and drug delivery device 12. Remote distribution link 42 provides a channel for downloading data from the patient over a telephone line or over the internet, for example. RF telemetry 44 provides immediate access to the data on a dedicated channel. Typically, a patient is required to visit the physician's office when data are to be downloaded via RF telemetry 44. In some embodiments of the present invention, collected ePAD values, delivered drugs, dosages, delivery dates, delivery times and the like can be downloaded from the patient, and can then be processed as events, trends, or the like.

The information exchanged may include programming instructions. Processor 26 may be programmable by a physician via input/output devices 42 and 44. Memory 28 may be used to store the instructions programmed by the physician. The programming may reflect, for example, the physician's judgment as to the appropriate drugs and dosages for the one or more drugs to be delivered to a patient over a range of ePAD values. The programming may also reflect, for example, the physician's judgment as to the appropriate drugs and dosages for the one or more drugs to be delivered in light of the determined activity level.

The correspondence between ePAD on the one hand, and drugs and dosages on the other could be stored in memory 28 as a look-up table that maps ePAD values or ranges of ePAD values to the appropriate drugs and dosages. When processor 26 receives a measured ePAD value via pressure signal 40 in such an embodiment, processor 26 then finds drugs and dosages corresponding to the measured pressure value by looking up the measured ePAD value in the table. The relationships between ePAD and dosages may also be described as curves, or as equations that defines curves.

In some embodiments of present invention where the patient's activity level is considered when deciding whether to modify the drug therapy, the activity level may be implemented as a threshold. For example, if the activity sensor output and/or the heart rate exceed a threshold value, the processor may disregard an elevated ePAD and control drug delivery device 12 to deliver the same drugs at the same dosages. In other embodiments, the correspondence between ePAD and activity level on the one hand, and drugs and dosages on the other could be stored in memory 28 as a look-up table that maps ePAD values, activity sensor output values, and heart rates to the appropriate drugs and dosages. When processor 26 receives a measured ePAD value via pressure signal 40, an activity sensor output 47, and a heart rate in such an embodiment, processor 26 then finds corresponding drugs and dosages by looking up the measured ePAD value, activity sensor output 47, and heart rate in the table. The relationships between ePAD, activity sensor output, heart rate, and dosages may also be described as curves, or as equations that defines curves.

FIGS. 5, 7 and 9 are for purposes of illustration. How drug selection and dosages correspond to measured ePAD values depends on the drug at issue. The correspondence may also depend upon the patient's particular needs and how well the drugs cooperate with one another.

The preceding specific embodiments are illustrative of the practice of the invention. It is to be understood, therefore, that other expedients known to those skilled in the art or disclosed herein may be employed without departing from the invention or the scope of the claims.

The invention further includes within its scope the methods of making and using the systems described above. These methods are not limited to the specific examples described above, but may be adapted to meet the needs of a particular patient. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

What is claimed is:

1. An implantable medical device comprising:
a pressure monitor that estimates a pulmonary artery diastolic pressure as a function of a pressure in a heart of a patient; and
a processor that selects one of a first dosage and a first dosage rate of a therapeutic drug that corresponds to the estimated pulmonary artery diastolic (EPAD) pressure to maintain said ePAD pressure within a range of approximately about 12 mmHg to about 18 mmHg and that selects one of a second dosage and a second dosage rate of the therapeutic drug for a ePAD within a second range, wherein the second range is different than the first range.

2. The device of claim 1, wherein the processor selects one of the first dosage, the first dosage rate, the second dosage, the second dosage rate from a look-up table.

3. The device of claim 1, wherein the processor selects at least one of the first dosage and the second dosage that corresponds to the estimated pulmonary artery diastolic pressure as a function of an equation that relates said first dosage and said second dosage to ePAD pressure.

4. The device of claim 1, wherein the device is implanted in the abdomen of a patient.

5. The device of claim 1, further comprising a pressure sensor that generates a pressure signal as a function of a pressure in the heart of the patient, and
wherein the pressure monitor estimates the pulmonary artery diastolic pressure as a function of the pressure signal.

6. The device of claim 5, wherein the pressure sensor includes one of a capacitive absolute pressure sensor, a piezoelectric crystal transducer and a piezoresistive pressure transducer.

7. The device of claim 5, wherein the pressure sensor is disposed in a right ventricle of the heart of the patient.

8. The device of claim 5, wherein the pressure monitor estimates the pulmonary artery diastolic pressure by identifying a pressure value at a point of maximum slope of the pressure signal.

9. The device of claim 5, wherein the pressure monitor comprises a differentiating circuit that generates a differential signal that is representative of a first derivative of the pressure signal, and
wherein the pressure monitor estimates the pulmonary artery diastolic pressure as a function of the differential signal.

10. The device of claim 5, wherein the pressure monitor comprises a differentiating circuit that generates a differential signal that is representative of a second derivative of the pressure signal, and
wherein the pressure monitor estimates the pulmonary artery diastolic pressure as a function of the differential signal.

11. The device of claim 1, further comprising a drug delivery device that delivers the selected dosage or selected dosage rate of the therapeutic drug to the patient, wherein the processor generates a control signal as a function of one of the selected dosage and the selected dosage rate, and wherein the drug delivery device receives the control signal and delivers the selected dosage or the selected dosage rate as a function of the control signal.

12. The device of claim 11, wherein the drug delivery device comprises:

a reservoir configured to receive and store the therapeutic drug; and an infusion apparatus that delivers the therapeutic drug to an infusion site in the body of the patient.

13. The device of claim 12, wherein the infusion site is one of the subclavian vein, superior vena cava and fatty tissue of the body of the patient.

14. The device of claim 12, wherein the drug delivery device further comprises a pump that delivers the therapeutic drug from the reservoir to a proximal end of the infusion apparatus.

15. The device of claim 11, wherein the therapeutic drug comprises a substance that increases cardiac output.

16. The device of claim 11, wherein the therapeutic drug comprises a substance that has a positive inotropic effect on the heart of the patient.

17. The device of claim 11, wherein the therapeutic drug includes one of digitalis, digoxin, digitoxin, dopamine, dobutamine, milrinone and amrinone.

18. The device of claim 1, further comprising an input/output device coupled to the processor, the input/output device configured to exchange information between a person and the processor.

19. A device according to claim 1, further comprising a drug delivery device delivers one of the selected dosage and the dosage rate of the therapeutic drug to the patient, said drug delivery device comprising:

a multi-chamber reservoir configured to receive and store at least two different therapeutic drugs;

wherein the processor generates a control signal as a function of one of the selected dosage and the dosage rate of each of said at least two different therapeutic drugs; and wherein the drug delivery device receives the control signal and delivers one of the selected dosage and the dosage rate of one of the at least two different therapeutic drugs as a function of the control signal.

20. A device according to claim 19, further comprising:

an infusion apparatus coupled to the multi-chamber reservoir and adapted to deliver the at least two different therapeutic drugs into at least one of: an organ, a volume of tissue, a cavity, and a vessel of the body of the patient.

21. A device according to claim 20, wherein the vessel comprises one of:

a subclavian vein, a superior vena cava vein, and an inferior vena cava; and wherein the volume of tissue comprises a volume of fatty tissue.

22. A device according to claim 19, wherein the drug delivery device further comprises a pump that delivers one of the at least two different therapeutic drugs from the multi-chamber reservoir to a proximal end of the infusion apparatus.

23. A device according to claim 19, wherein one of the at least two different therapeutic drugs comprise a substance that increases cardiac output.

24. A device according to claim 19, wherein one of the at least two different therapeutic drugs comprise a substance that provides a positive inotropic effect on the heart of the patient.

25. A device according to claim 19, wherein one of the at least two different therapeutic drugs includes one of: digitalis, digoxin, digitoxin, dopamine, dobutamine, milrinone, amrinone.

* * * * *